(12) United States Patent
Tsai et al.

(10) Patent No.: US 10,920,225 B2
(45) Date of Patent: Feb. 16, 2021

(54) ANTISENSE OLIGONUCLEOTIDE FOR SPLICING ADJUSTMENT OF MUTANT DOPA DECARBOXYLASE GENE AND USING METHOD THEREOF

(71) Applicant: Taichung Veterans General Hospital, Taichung (TW)

(72) Inventors: Chi-Ren Tsai, Taichung (TW); Ching-Shiang Chi, Taichung (TW); Hsiu-Fen Lee, Taichung (TW)

(73) Assignee: TAICHUNG VETERANS GENERAL HOSPITAL, Taichung (TW)

( * ) Notice: Subject to any disclaimer, the term of this patent is extended or adjusted under 35 U.S.C. 154(b) by 210 days.

(21) Appl. No.: 15/585,410

(22) Filed: May 3, 2017

(65) Prior Publication Data

US 2017/0321217 A1 Nov. 9, 2017

Related U.S. Application Data

(60) Provisional application No. 62/330,894, filed on May 3, 2016.

(51) Int. Cl.
*C12N 15/11* (2006.01)
*C12N 15/113* (2010.01)

(52) U.S. Cl.
CPC .. *C12N 15/1137* (2013.01); *C12Y 401/01028* (2013.01); *C12N 2310/11* (2013.01); *C12N 2320/33* (2013.01)

(58) Field of Classification Search
CPC .................................................. C12N 15/1137
See application file for complete search history.

(56) References Cited

U.S. PATENT DOCUMENTS

| | | | | |
|---|---|---|---|---|
| 2004/0023383 A1* | 2/2004 | Bhanot | .................. | C07H 21/04 435/375 |
| 2006/0134663 A1* | 6/2006 | Harkin | .................. | C12Q 1/6837 435/6.11 |
| 2007/0054278 A1* | 3/2007 | Cargill | .................. | C12Q 1/6827 435/6.11 |
| 2007/0072175 A1* | 3/2007 | Cooper | ................ | C12Q 1/6876 435/5 |

FOREIGN PATENT DOCUMENTS

WO WO-03022227 A2 * 3/2003 ......... C12N 15/1138

OTHER PUBLICATIONS

Rosen et al, WO-0157182-A2, Aug. 2001, only 30 relevant pages out of 3071 included. (Year: 2001).*
GenBank AY526322.1, 2004, pp. 1-59 (Year: 2004).*
Eisen and Smith, "Controlling morpholino experiments: don't stop making antisense," Development 135, 1735-1743 (2008).
Moulton, "Making a Morpholino Experiment Work: Controls, Favoring Specificity, Improving Efficacy, Storage, and Dose," Morpholino Oligomers: Methods and Protocols, Methods in Molecular Biology, vol. 1565, DOI 10.1007/978-1-4939-6817-6_2 (2017).
Sahu, Shilakari, Nayak, Kohli, "Antisense Technology: A Selective Tool for Gene Expression Regulation and Gene Targeting," Current Pharmaceutical Biotechnology, 2007, 8, 291-304.
Sharma, Sharma, Singh, "Antisense oligonucleotides: modifications and clinical trials," Royal Society of Chemistry, www.rsc.org/medchemcomm (Aug. 2014).
Aboul-Fadl, "Antisense Oligonucleotides: The State of the Art," Current Medicinal Chemistry, 2005, 12, 2193-2214.
Lingamanaidu V. Ravichandran, Nicholas M. Dean, and Eric G. Marcusson, "Use of Antisense Oligonucleotides in Functional Genomics and Target Validation, " Oligonucleotides 14:49-64, Mary Ann Liebert, Inc. (2004).
Geary, Norris, Yu, Bennett "Pharmacokinetics, biodistribution and cell uptake of antisense oligonucleotides," Advanced Drug Delivery Reviews 87 (2015) 46-51.

* cited by examiner

*Primary Examiner* — Ekaterina Poliakova-Georgantas
(74) *Attorney, Agent, or Firm* — Bacon & Thomas, PLLC

(57) ABSTRACT

This present invention discloses an antisense oligonucleotide for splicing adjustment of mutant dopa decarboxylase gene which is complementary to SEQ ID NO: 1. This antisense oligonucleotide can modulate alternative splicing site of mutant dopa decarboxylase gene. It is helpful to research and develop drug to treat AADC deficiency symptom. This present invention also discloses a method to use said antisense oligonucleotide in vitro.

4 Claims, 18 Drawing Sheets

Specification includes a Sequence Listing.

FIG. 8 tcagatggca acttcgccat gcgtgcgtct gccctgcagg AAGCCCTGGA
                                    Exon 6 | Intron 6    ASO-6e (SEQ ID NO. 10)
GAGAGACAAA GCGGGCTGGCC TGATTCCTTT CTTTTGTAAGT TCGGCAGCAC
                                    ASO-6s (SEQ ID NO. 11)    ASO-A~AA (SEQ ID NO. 2~6, 15~36)
TTGTTGGCTCC TGGCCAATAA GGTGAAACTC CGTCTCTACT AAAAATACAA AAAAAAATTA GCCGGGGCATG GTGGCGCATT CTTGTAATCC CAGCTACTCG
ASO-9AA (SEQ ID NO. 9)
GGAAGCTGAG GCAGGAGAAT GGCGTGAACC CGGGAGGCGG AGGTTGCAGT

GAGCCGAGAT CGCGCCGCTG CACTCCCAGCC TGTGTGACAG AGCAAGACTC

TGTCTCAAAA AAAATTAATC TTTGAGAAAC GCTTTTTACC TCCATTTTTT

TTTTTGTTTT GTCAATTCAA GTCAATTCCA CAGTGTAATG TGGAAGAACT
        ASO-6as (SEQ ID NO. 7)                          ASO-6ae (SEQ ID NO. 8)
+324
GACATGGCtc aaagttagca cgcagagcaa ggtgacagcc aagacatttt

FIG. 9

ANTISENSE OLIGONUCLEOTIDE FOR SPLICING ADJUSTMENT OF MUTANT DOPA DECARBOXYLASE GENE AND USING METHOD THEREOF

BACKGROUND OF THE INVENTION

Field of the Invention

The present invention relates to an antisense oligonucleotide, more particularly to an antisense oligonucleotide for splicing adjustment of mutant dopa decarboxylase gene and using method thereof.

Description of the Prior Art

Aromatic L-amino acid decarboxylase (AADC) is a synthetase of dopamine, the human neurotransmitter, and serotonin. The key of AADC is dopa decarboxylase (DDC) gene which has 15 exons. AADC deficiency is a rare recessive hereditary disorder. Inventors' research at 2009 found that the most AADC deficiency cases in Taiwan are an A-to-T mutation downstream of fourth nucleotides (+4) from the splicing site of intron 6 of DDC gene, briefly name IVS6+4A>T mutation. A pre-mRNA of DDC gene splices at a wrong slicing site (+38 cryptic splice site) because of the IVS6+4A>T mutation. It makes extra 37 base pair of nucleotides inserted into intron 6 after exon 6 of mRNA of mutant DDC gene. Therefore, the IVS6+4A>T mutation will cause aberrant gene splicing.

Antisense oligonucleotides (ASOs) is a kind of artificial syntheses single strand DNA or RNA molecular with about 13-45 nucleotides which can hybridize to the complement mRNA sequence to repress transcription into protein of said mRNA. On the other hand, former studies reported that different types of ASO can adjust aberrant gene splicing successfully by delivering it into cells.

Developing ASOs for adjusting, even fixing, aberrant DDC gene splicing is helpful to research drugs for AADC deficiency symptom treatment. ASOs for the IVS6+4A>T mutation are more helpful for research drugs of AADC deficiency symptom in Taiwan. Therefore, this present invention design specific sequence of ASOs to adjust splicing site of IVS6+4A>T mutation DDC gene.

SUMMARY OF THE INVENTION

The objective of this present invention is to provide an antisense oligonucleotide which can adjust splicing of IVS6+4A>T mutant dopa decarboxylase gene.

In order to achieve the objective, this present invention reveals an antisense oligonucleotide for splicing adjustment of mutant dopa decarboxylase gene which is complementary to SEQ ID NO: 1.

In another example of this present invention, the mutation type of mutant dopa decarboxylase gene is IVS6+4A>T.

In another example of this present invention, it can increase serotonin levels in the IVS6+4A>T mutant cells and the sequence may be one of SEQ ID NO: 2, 3, 4, 5 or 6.

In another example of this present invention, it can modulate the pattern of splicing isomers of IVS6+4A>T mutant dopa decarboxylase gene and the sequence may be one of SEQ ID NO: 7, 8 or 9.

In another example of this present invention, it can decrease aberrant splicing isomers of IVS6+4A>T mutant dopa decarboxylase gene, wherein the isomer is 5-6+37-7-8 fragment and the sequence may be one of SEQ ID NO: 10, 11, 12 or 14.

Another objective of this present invention is to provide a method of using an antisense oligonucleotide to adjust splicing of IVS6+4A>T mutant dopa decarboxylase gene.

In order to achieve the objective, this present invention also provides a method of using an antisense oligonucleotide for splicing adjustment of mutant dopa decarboxylase gene by adding any one of the antisense oligonucleotide from above-mentioned antisense oligonucleotide to IVS6+4A>T mutant cells for cultivation.

Therefore, this present invention reveals an antisense oligonucleotide and a method using thereof to adjust splicing of IVS6+4A>T mutant dopa decarboxylase gene.

BRIEF DESCRIPTION OF THE DRAWINGS

FIG. 8 shows designed 29 ASOs sequences based on the complementary target of DDC gene intron 6.

FIG. 9 shows all ASOs sequences and positions disclosed in this present invention.

DETAILED DESCRIPTION OF THE EMBODIMENT OF THE INVENTION

Figure 1A:
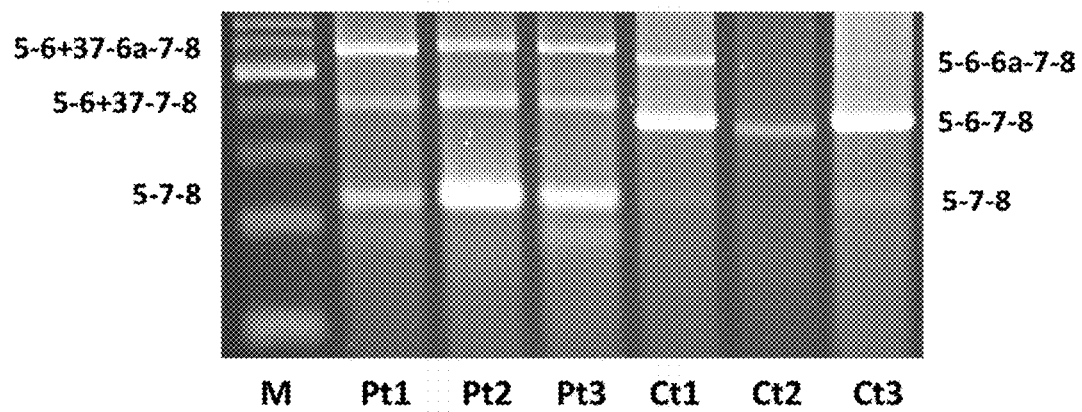
FIG. 1A is a represented electrophoresis gel photograph shows mRNA isoforms from cells obtained from IVS6+4 A>T mutant of AADC deficiency patients (Pt) and normal (Ct), wherein identified positions of possible isoforms between exon 5 to 8 of DDC gene.

Following contents illustrate related experiment methods in this present invention, wherein levels of mRNA isoform is compared with all mRNA levels and shown as percentage. Because of conventional ASOs will rapidly degenerate by endonucleases or exonucleases after entering into cells. Therefore, morpholino ASOs replace conventional ASOs in this present invention. Morpholino ASO has morpholine ring replacing deoxyribose ring of conventional ASO which becomes stable and has better efficiency and specificity.

Experiment 1: Cell Culture

Human lymphoblastoid cells obtained from normal controls and homozygous for the IVS6+4 A>T mutation of AADC deficiency patients were grown in RPMI-1640 medium containing 20% fetal bovine serum, 100 U/ml penicillin, 100 μg/ml streptomycin, and 0.25 μg/ml amphotericin B. Cells were incubated at 37° C. in a 5% $CO_2$ atmosphere. All media and chemicals were purchased from HyClone (GE Healthcare Life Sciences, USA).

Experiment 2: Transfection of Cells with ASOs

Cells ($8\times10^6$ cells/ml) were transfected with 10-30 μM ASOs using 8 μM Endoporter (Genetools, USA) in RPMI-1640 medium containing fetal bovine serum.

ASOs in this present invention are as followings:

| Name | Sequence | SEQ ID NO |
|---|---|---|
| ASO-D | TTGGCCAGGAGCCACAAGTGCTGCC | 2 |
| ASO-K | CACCTTATTGGCCAGGAGCCACAAG | 3 |
| ASO-R | GGAGTTTCACCTTATTGGCCAGGAG | 4 |
| ASO-W | GAGACGGAGTTTCACCTTATTGGCC | 5 |
| ASO-AA | AGTAGAGACGGAGTTTCACCTTATT | 6 |
| ASO-6as | TGTGGAATTGACTTGAATTGACAAA | 7 |
| ASO-6ae | GCCATGTCAGTTCTTCCACATTACA | 8 |
| ASO-9AA | CACCATGCCCGGCTAATTTTTTTTT | 9 |
| ASO-6e | CCGCTTTGTCTCTCTCCAGGGCTTC | 10 |
| ASO-6s | ACAAGTGCTGCCGAACATACAAAGA | 11 |
| TB30 | GCTCGTCCGCCCAGCCCGACATC | 12 |
| TB40 | CGATGAATACCCGACAGCCACTCAT | 13 |
| TB55 | ACCCAAGGGCTGGTTGTCGAACGGC | 14 |
| ASO-A | AAGCCGTCGTGAACACCGAGGACCG | 15 |
| ASO-B | AGCCGTCGTGAACACCGAGGACCGG | 16 |
| ASO-C | GCCGTCGTGAACACCGAGGACCGGT | 17 |
| ASO-E | CGTCGTGAACACCGAGGACCGGTTA | 18 |
| ASO-F | GTCGTGAACACCGAGGACCGGTTAT | 19 |
| ASO-G | TCGTGAACACCGAGGACCGGTTATT | 20 |
| ASO-H | CGTGAACACCGAGGACCGGTTATTC | 21 |
| ASO-I | GTGAACACCGAGGACCGGTTATTCC | 22 |
| ASO-J | TGAACACCGAGGACCGGTTATTCCA | 23 |
| ASO-L | AACACCGAGGACCGGTTATTCCACT | 24 |
| ASO-M | ACACCGAGGACCGGTTATTCCACTT | 25 |
| ASO-N | CACCGAGGACCGGTTATTCCACTTT | 26 |
| ASO-O | ACCGAGGACCGGTTATTCCACTTTC | 27 |
| ASO-P | CCGAGGACCGGTTATTCCACTTTCA | 28 |
| ASO-Q | CGAGGACCGGTTATTCCACTTTCAG | 29 |
| ASO-S | AGGACCGGTTATTCCACTTTCAGGC | 30 |
| ASO-T | GGACCGGTTATTCCACTTTCAGGCA | 31 |
| ASO-U | GACCGGTTATTCCACTTTCAGGCAG | 32 |
| ASO-V | ACCGGTTATTCCACTTTCAGGCAGA | 33 |
| ASO-X | CGGTTATTCCACTTTCAGGCAGAGA | 34 |
| ASO-Y | GGTTATTCCACTTTCAGGCAGAGAT | 35 |
| ASO-Z | GTTATTCCACTTTCAGGCAGAGATG | 36 |

Experiment 3: RNA Isolation and Quantitative RT-PCR Analysis of Human DDC mRNA Total RNA was extracted from cultured cells using Tri Reagent (Molecular Research Center, USA.). Quantitative RT-PCR was performed using 500 ng RNA samples using Superscript III reverse transcriptase (Invitrogen Co., USA) wherein exon 5 to exon 8 of the DDC mRNA sequence was then PCR amplified for analysis. Briefly, the RT step was performed at 55° C. for 60 mM, followed by PCR at 95° C. for 30 s, 60° C. for 30 s, and 72° C. for 50 s for 30 cycles. The resulting RT-PCR products were separated by 2% agarose gel electrophoresis, stained with GelGreen (Biotium, Inc., USA), and visualized using blue-light Box. The band intensity was calibrated using a low DNA mass ladder (Invitrogen) and calculated densitometrically using AlphaView SA image analysis software (Protein Simple, USA).

Experiment 4: Protein Isolation and Western Blot Analysis

Three Ser/Arg-rich protein (SR protein), SRp30c, SRp40 and SRp50, were extracted from ASO-treated cells. 40 μg of each homogenate was mixed with an equal amount of 2× standard SDS sample loading buffer containing 125 mM Tris-HCl (pH 6.8), 4% SDS, 20% glycerol, 10% β-mercaptoethanol, and 0.25% bromophenol blue and boiled for 10 min before electrophoresis. Proteins were separated by 12% SDS-PAGE and transferred by electroblotting onto PolyScreen PVDF transfer membrane (Merck Millipore). The membrane was then treated sequentially with blocking solution (phosphate-buffered saline (PBS) containing 5% skim milk), then with appropriate diluted antibody of SRp30c (Proteintech group, Manchester, UK), SRp40 (MBL, Nagoya, Japan) and SRp55 (Santa Cruz Biotechnology, Texas), and with goat anti-rabbit IgG (H+L) polyclonal antibody conjugated to peroxidase (Jackson, Pa., USA). After washing, the immunoreactivity was visualized using the Immobilon Western HRP Substrate (EMD Millipore, Darmstadt, Germany) Band results were imaged by ImageQuant LAS 4000 (GE Healthcare, Bucks, UK).

Experiment 5: Serotonin Measurement

The levels of serotonin in cells were determined using an enzyme immunoassay system (Serotonin high sensitivity ELISA; IBL, Germany), according to the manufacturer's protocol. Briefly, cells were collected and extracted with IP lysis buffer. The supernatants of the resulting cell extracts were then subjected to ELISA analysis. A non-linear regression model was used for curve fitting, as recommended by the manufacturer. A two-tailed Student's t-test was conducted to compare serotonin levels between ASO-treated cells and scramble control oligo-treated cells.

Experiment 6: DDC Protein Detection

Intracellular DDC protein levels were determined by PEA using the Proseek Assay Development kit (Olink Bioscience, Sweden), according to the manufacturer's protocol. Cells were collected and protein was extracted using IP lysis buffer, and the supernatants of the resulting cell extracts were harvested for PEA. Oligo A and the Oligo B were conjugated to polyclonal human DDC antibodies (R&D Systems, USA) to create Proseek probe A and probe B for the DDC protein, respectively. Then, a probe master mixture was prepared by mixing Proseek probes A and B in Assay Solution. Next, 3 μl probe master mixture and 1 μl cell extract were transferred to a reaction tube and incubated for 2 h at room temperature. For the probe extension step, the reaction tube was incubated for 5 min at 37° C. in a preheated thermal cycler, after which 76 μl of the Pre-Extension master mixture was added and incubated for 5 min at 37° C. After incubation, 20 μl Extension master mixture containing Extension Polymerase was added and the reaction was incubated for 20 min at 37° C. for polymerization, followed by 10 min at 85° C. for inactivation of the Extension Polymerase. Lastly, real-time PCR was performed using a Rotorgene 6000 instrument (Corbett Research, Australia) with the following thermal cycling conditions: one cycle of 95° C. for 5 min, followed by 45 cycles at 95° C. for 15 s and 60° C. for 1 min.

Experiment 7: In Silico Predictions

Putative splicing regulatory elements were predicted using SpliceAid (http://www.in-troni.it/splicing.html), ESRsearch (http://ibis.tau.ac.il/ssat/ESR.htm), and ESEfinders (http://rulai.cshl.edu/cgi-bin/tools/ESE3/esefinder.cgi?process=home) software. In silico analysis of the splice site strength was assessed using MaxEntScan Web-based tools (http://genes.mit.edu/burgelab/maxent/Xmaxentscan_scoreseq.html).

Result 1: Expression Patterns in Isolated Lymphoblastoid Cells of Normal Controls and AADC IVS6+4 A>T Patients Obtaining lymphoblastoid cells from normal controls (Ct1-Ct3) and AADC deficiency patients causing by IVS6+4 A>T mutant (Pt1-Pt3) by Experiment 1. DDC gene splicing patterns were analyzed by Experiment 3.

Figure 1B:
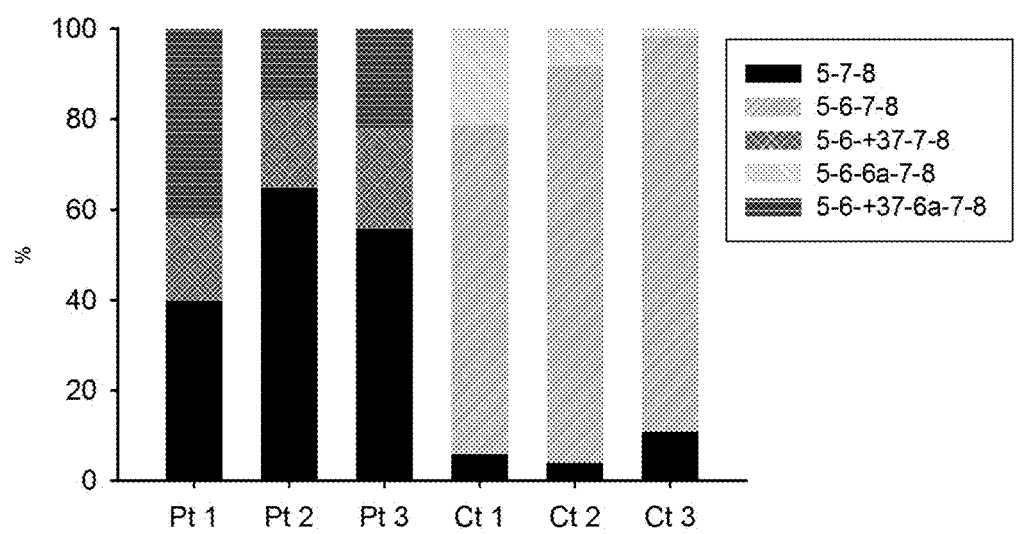
FIG. 1B is quantification of FIG. 1A.

As shown in FIGS. 1A and 1B, DDC gene from normal cells had the most ratio of splicing isoform 5-6-7-8, and there included minor-expressed isoform 5-6-6a-7-8 with a new exon 6a and isoform 5-7-8. DDC gene from IVS6+4 A>T mutant cells had the most ratio of splicing isoform 5-7-8, and there included aberrant isoform 5-6+37-7-8 and 5-6+37-6a-7-8 with an extra 37 bases of nucleotide after exon 6. One thing need to be noticed was that the isoform 5-7-8 means gene spliced over exon 6-37 or exon 6. Besides, there includes isoform 5-7-8 in the normal cells, but the ratio of it was under 11%.

Figure 1C:
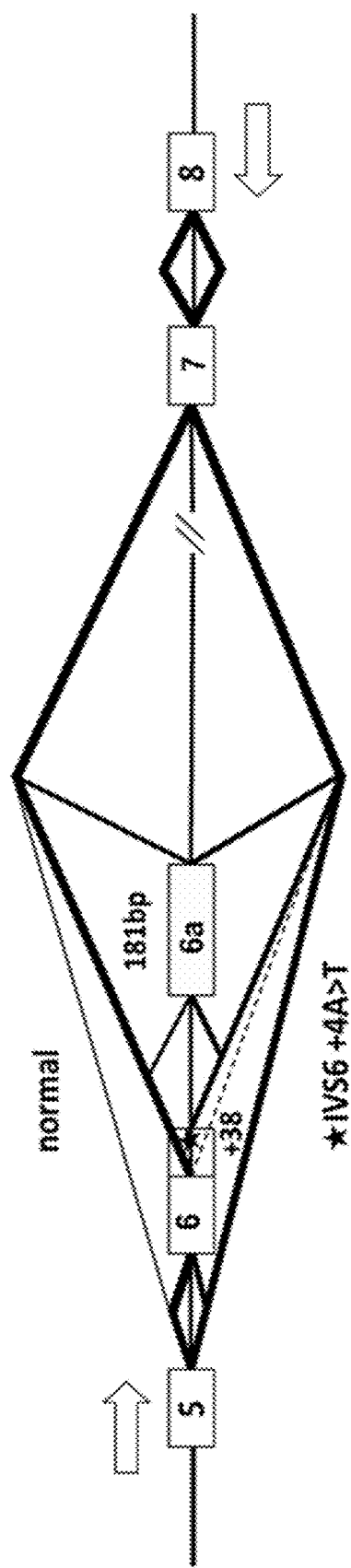
FIG. 1C demonstrates alternative splicing pattern of DDC gene exon 5 to 8.

FIG. 1C represents the putatively alternative splicing patterns of DDC gene based on the result of FIG. 1B. Lines in the FIG.s connect spliced mRNA isoforms of DDC gene, and the thickness of these lines means the higher splicing tendency of this way.

Figure 8:
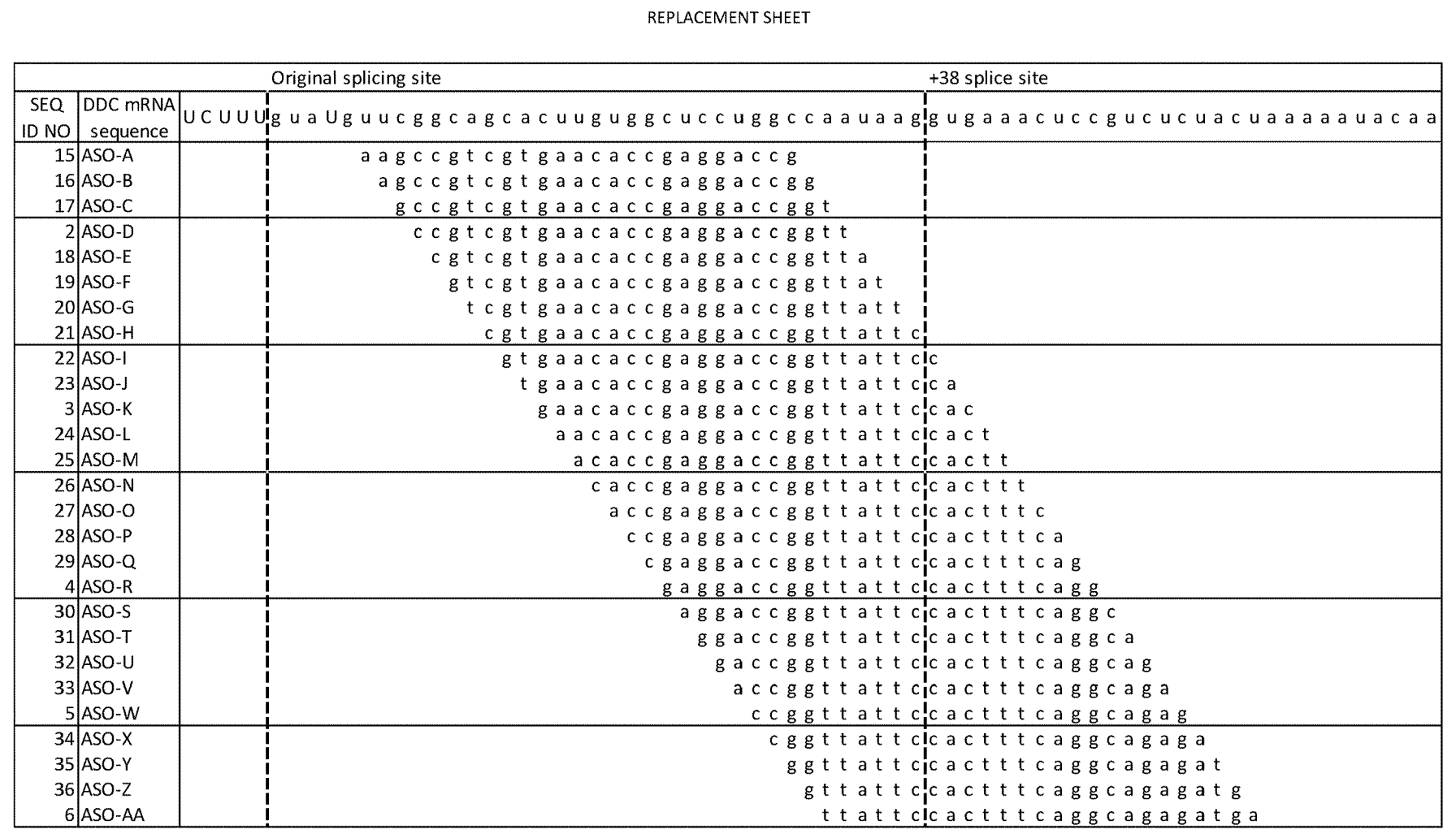

Result 2: ASOs Adjust the Aberrant Gene Splicing Induced by the IVS6+4 A>T Mutation in Lymphoblastoid Cells of Patients with AADC Deficiency ASOs with 25-mer designed by this present invention were obtained from Genetools (Philomath, Oreg., USA). There are four kinds of ASOs. Class 1 ASOs are the reverse complement sequences targeting on exon 6 of DDC gene. These complementary sequences selected by micro-walk analysis downstream with one base from 5' splicing site of exon 6, the border between exon 6 and intron 6, till covering to the wrong splicing site, +38 cryptic splice site, of the IVS6+4 A>T mutation of DDC gene. Additionally considering ASO-targeting binding energy or melting temperature (Tm) and RNA secondary structure, there are 29 suitable ASOs for number A-2, A-1, A~Z and AA. Specific sequences are shown at FIG. 8.

Besides, the present invention used a scramble control of the same length and vector with the ASOs but random sequences to verify the function of ASOs.

Figure 2A:
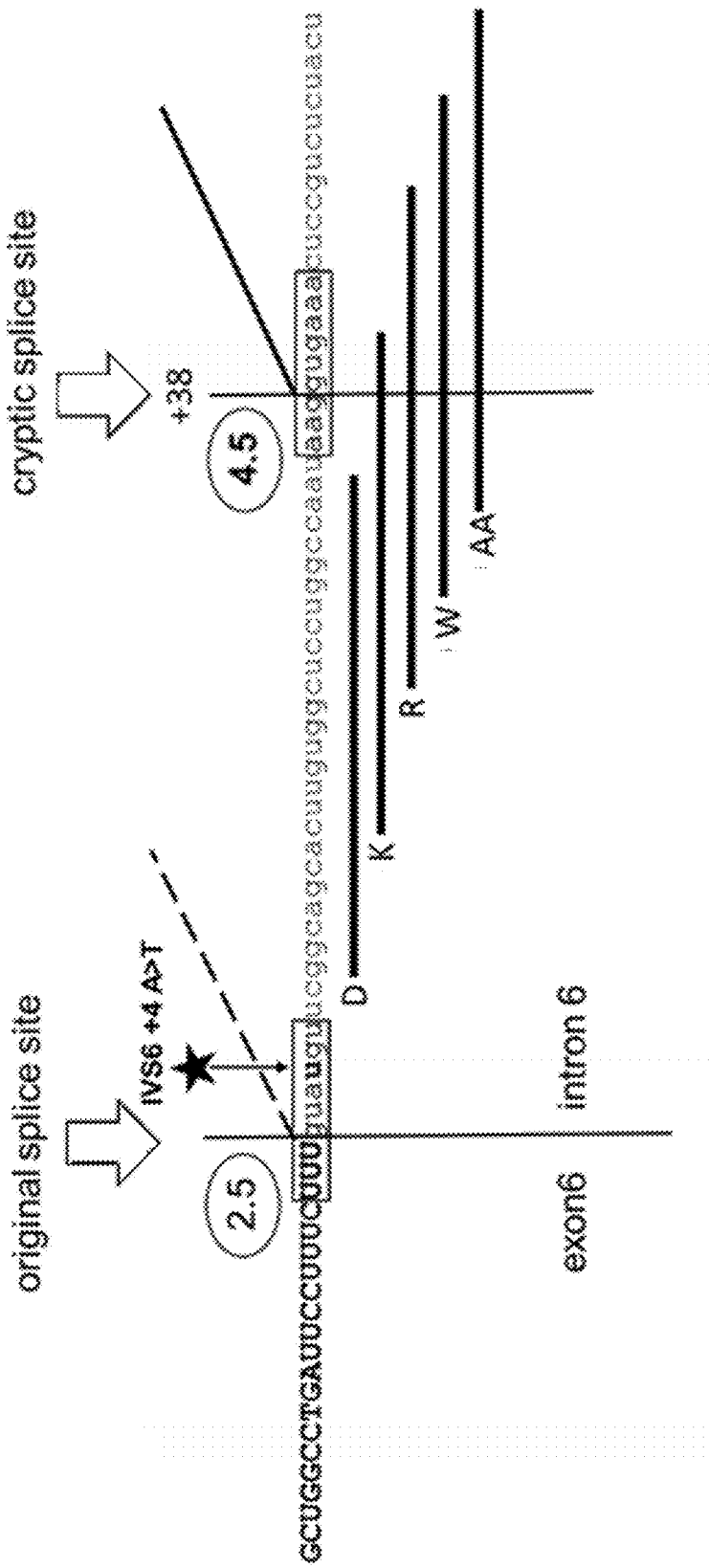
FIG. 2A shows complementary position of ASOs on DDC gene.

Preparing cells according to Experiment 1 and then five ASOs, ASO-D, ASO-K, ASO-R, ASO-W and ASO-AA were selected form the above-mentioned 29 ASOs for further Experiment 2, 3 to prove the effect of adjusting the splicing of DDC gene with IVS6+4 A>T mutation. The location of these five ASOs complements with DDC gene was shown at FIG. 2A.

Figure 2B:
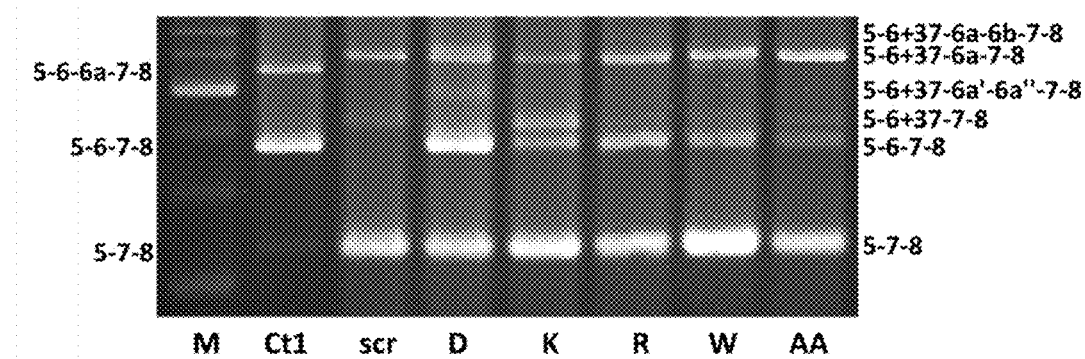
FIG. 2B is a represented electrophoresis gel photograph shows mRNA isoforms in the IVS6+4 A>T mutant cells after treatment of ASOs, wherein identified positions of possible isoforms between DDC gene 5 to 8.
Figure 2C:
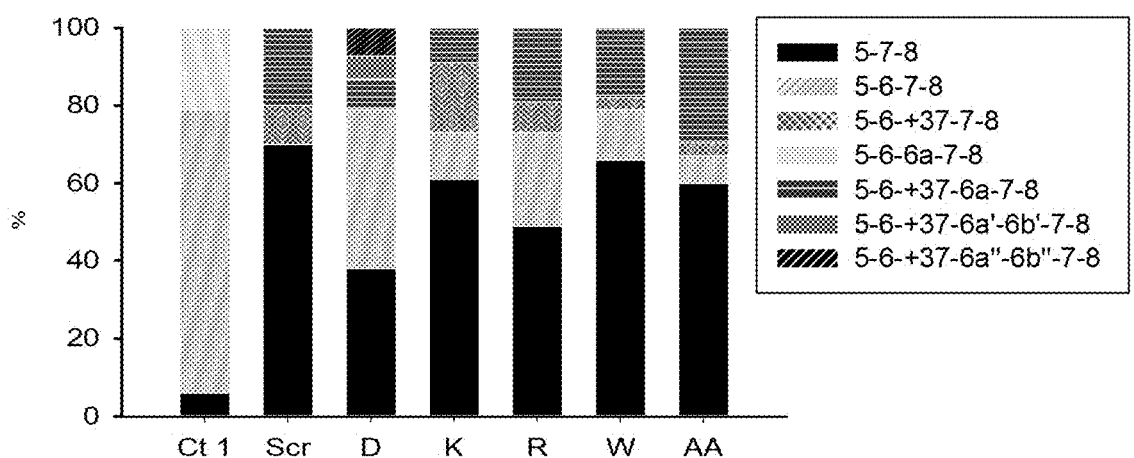
FIG. 2C is quantification of FIG. 2B.

Each of these five ASOs were subsequently transfected into the IVS6+4A>T mutant cells, respectively, at a concentration of 30 μM for 72 h. The result of quantitative RT-PCR showed that all five ASOs can yield restoration of the normal splicing isoform in IVS6+4A>T mutant cells (isoform 5-6-7-8 in the FIGS. 2B and 2C). Ten independent repeat operation concluded the restoration potential which normal splicing isoform percentage divides aberrant splicing isoform (5-6+37-7-8) percentage, of these five ASOs. ASO-AA restored the production of the normal isoform 5-6-7-8 from 0% to 7% of total transcripts, while retaining the aberrant splice isoform 5-6+37-7-8 at 3.5% of total transcripts, yielding a restoration ratio of 2:1. ASO-W restored the production of the normal isoform 5-6-7-8 to 13% of total transcripts, while retaining the aberrant splice isoform 5-6+37-7-8 at 3% of total transcripts, yielding a restoration ratio of 4.3:1. ASO-R restored the production of the normal isoform 5-6-7-8 to 24% of total transcripts, while retaining the aberrant splice isoform 5-6+37-7-8 at 8% of total transcripts, yielding a restoration ratio of 3:1. ASO-K restored the production of the normal isoform 5-6-7-8 to 12% of total transcripts, while retaining the aberrant splice isoform 5-6+37-7-8 at 18% of total transcripts, yielding a restoration ratio of 0.7:1. ASO-D restored the production of the normal isoform 5-6-7-8 to 41% of total transcripts, while reducing the aberrant splice isoform 5-6+37-7-8 to 0% of total transcripts. Therefore, ASO-D restored aberrant splice of DDC gene with IVS6+4 A>T mutation. However, ASO-D also created two new aberrantly spliced isoforms, 5-6+37-6a-6b-7-8 and 5-6+37-6a'-6a''-7-8, which comprised at 7.81% and 3.6% of the total transcripts, respectively. Furthermore, ASO-R and ASO-D both reduced the proportion of isoform 5-7-8 as compared to the scramble control. Wherein, ASO-R reduced the proportion of isoform 5-7-8 to 49% of the total transcripts, ASO-D reduced the proportion of isoform 5-7-8 to 38% of the total transcripts.

Taken together, all above-mentioned ASO-D, ASO-K, ASO-R, ASO-W and ASO-AA can adjust aberrant splice isoform 5-6+37-7-8, produce normal splice isoform 5-6-7-8 and reduce isoform 5-7-8.

Figure 2D:
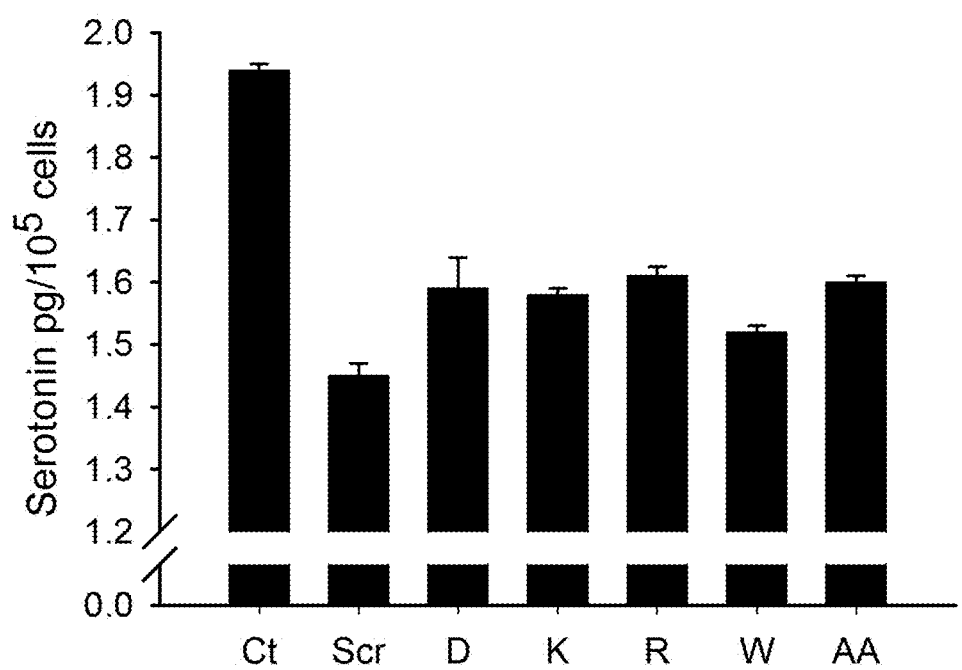
FIG. 2D shows increasing serotonin levels in the IVS6+4 A>T mutant cells after treatment of ASOs.

Serotonin levels of the IVS6+4 A>T mutation cells were tested through Experiment 5 and results were shown at FIG. 2D. It indicated that comparing to the cells transfected by control group, the cells transfected by the five ASOs produced more serotonin and illustrated that the class 1 ASOs can improve deficient production of serotonin by adjusting aberrant splicing of DDC gene.

Figure 3A:
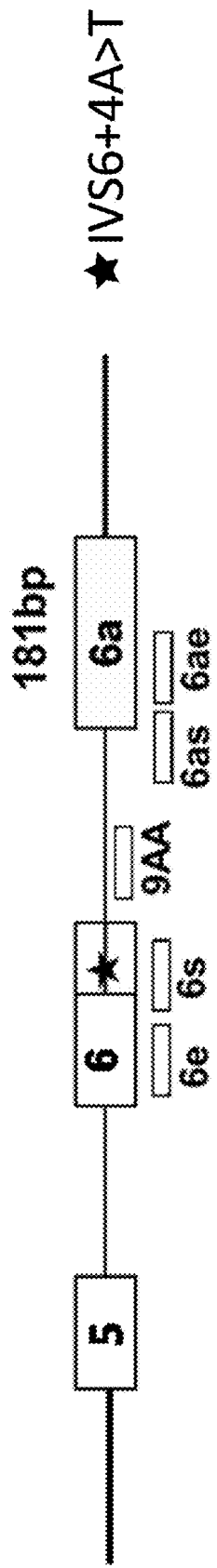
FIG. 3A shows complementary position of ASOs on DDC gene.

Result 3: Blockage of Exon 6a Increases the Expression Level of Isoform 5-6+37-7-8 in IVS6+4A>T Mutant Cells Based on above-mentioned results, this present invention designed class 2 ASOs which hybridize new exon 6a as target. Referring to FIG. 3A, ASO-6as was complement sequence bound to 5' splice donor site of intron 6. ASO-6ae was complement sequence bound to downstream putative exonic splicing enhancers (ESEs) in 5' splice donor site of intron 6a.

Figure 3B:
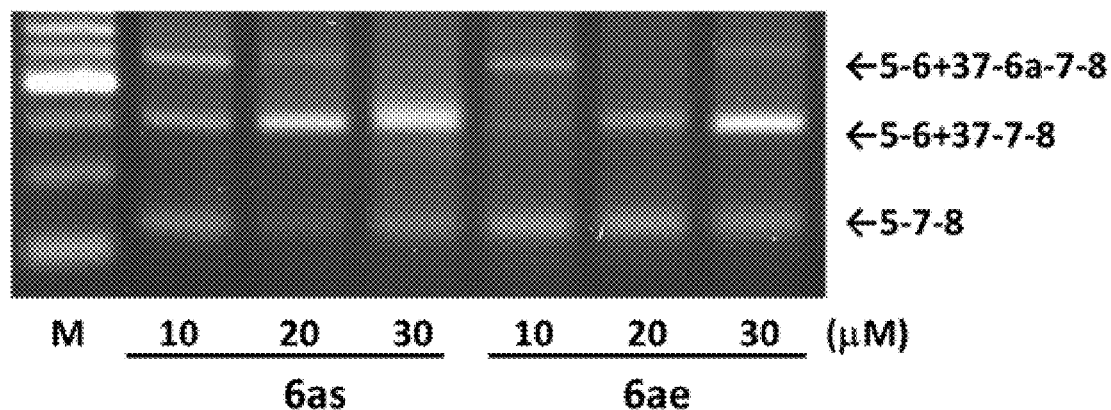
FIG. 3B is a represented electrophoresis gel photograph shows mRNA isoforms in the IVS6+4 A>T mutant cells after treatment of different concentration of ASOs, wherein identified positions of possible isoforms between DDC gene 5 to 8.
Figure 3C:
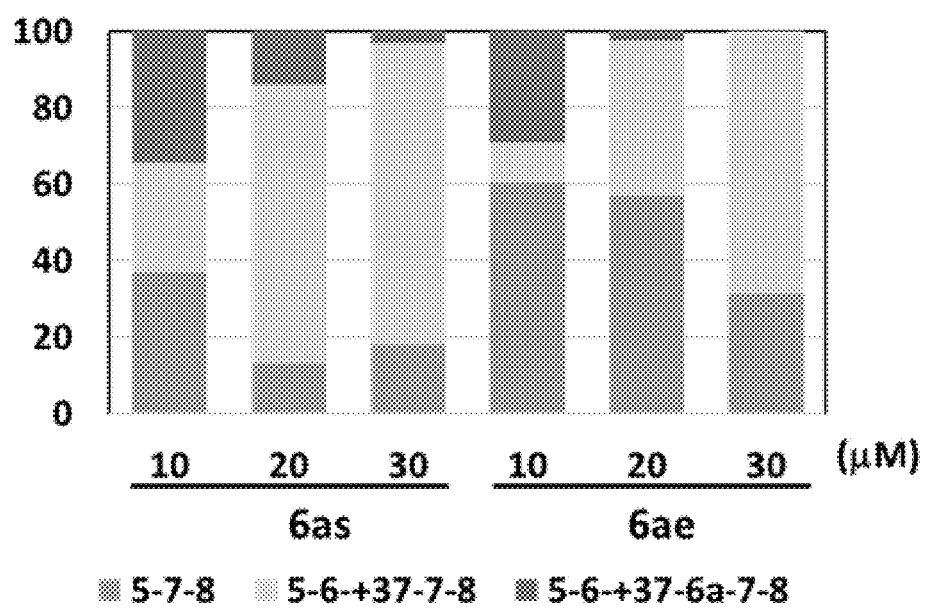
FIG. 3C is quantification of FIG. 3B.

Results from Experiment 1 to 3 were shown at FIG. 3B, 3C. Treatment with either ASO-6as or 6ae in 10 μM, 20 μM and 30 μM resulted in reductions of isoform 5-6+37-6a-7-8, and there were concentration-dependent effect. Production of isoform 5-6+37-6a-7-8 was from 34% to 1.3% of the total transcripts by comparison of 10 μM to 30 μM of ASO-6as. Production of isoform 5-6+37-6a-7-8 was from 18% to 0% of the total transcripts by comparison of 10 μM to 30 μM of ASO-6ae. But, ASO-6as and ASO-6ae increased aberrant isoform 5-6+37-7-8. For example, production of isoform 5-6+37-7-8 was 30% of the total transcripts by treatment of 10 μM ASO-6as, and production of isoform 5-6+37-7-8 increased to 77% of the total transcripts by treatment of 30 μM ASO-6as. Production of isoform 5-6+37-7-8 was 10% of the total transcripts by treatment of 10 μM ASO-6ae, and production of isoform 5-6+37-7-8 increased to 64% of the total transcripts by treatment of 30 μM ASO-6ae. Besides, treatment of ASO-6as and ASO-6ae can decrease isoform 5-7-8. For example, production of isoform 5-7-8 increased from 37% to 13% of the total transcripts by treatment of ASO-6as, and production of isoform 5-7-8 increased from 60% to 31% of the total transcripts by treatment of ASO-6ae.

Result 4: Use of Blocking ASOs to Define the Sequences that Modulate the Inclusion or Exclusion of Exon 6+37 Aberrant Splicing This present invention designed class 3 ASOs which hybridize mutant isoform exon 6+37 as target. Referring to FIG. 3A, ASO-6s was complement sequence bound to 5' splice site of intron 6. ASO-6e was complement sequence bound to ESEs of exon 6 simulated by computer.

Figure 3D:
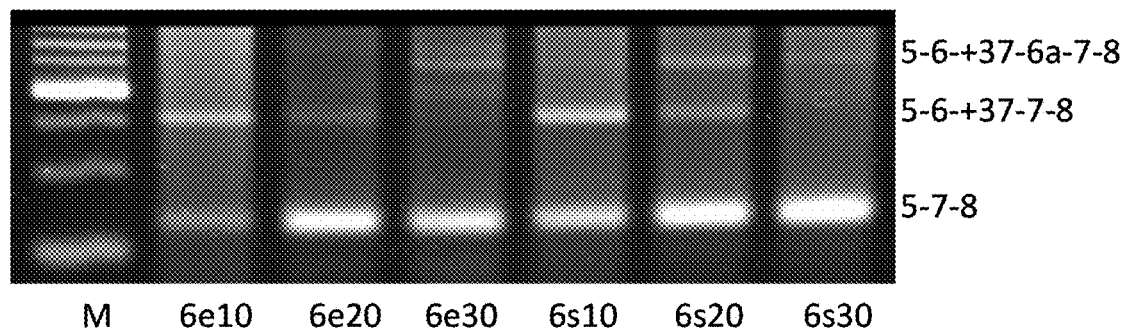
FIG. 3D is a represented electrophoresis gel photograph shows mRNA isoforms in the IVS6+4 A>T mutant cells after treatment of different concentration of ASOs, wherein identified positions of possible isoforms between DDC gene 5 to 8.
Figure 3E:
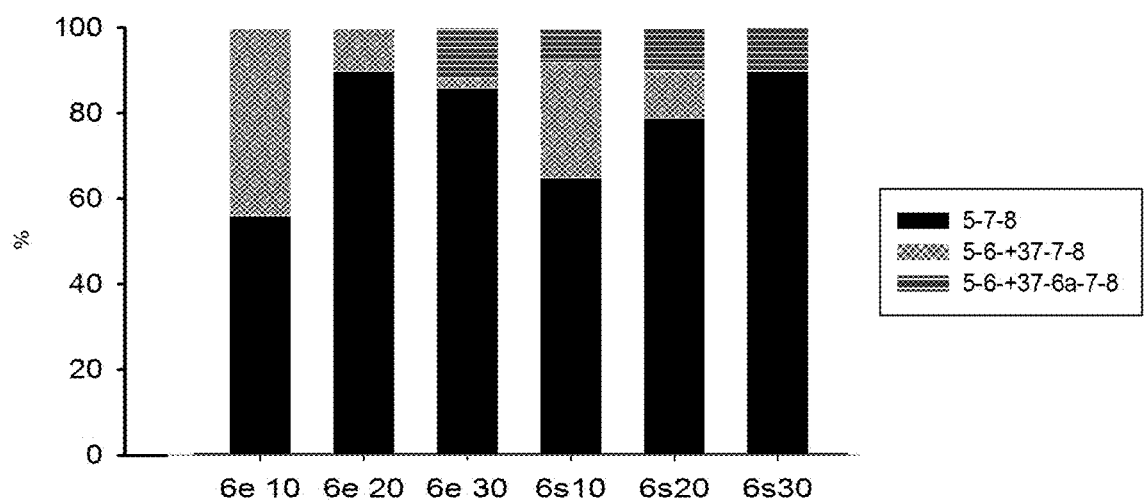
FIG. 3E is quantification of FIG. 3D.

Results from Experiment 1 to 3 were shown at FIG. 3D, 3E. Treatment of two ASOs decreased the proportions of isoform 5-6+37-7-8 and increased isoform 5-7-8. For example, proportion of aberrant isoform 5-6+37-7-8 was 31%, isoform 5-7-8 was 68% of the total transcripts under treatment of 10 μM ASO-6e. Treatment of 30 μM ASO-6e decreased the proportions of isoform 5-6+37-7-8 to 2.4% and increased 5-7-8 to 86%, but yielded the proportions of isoform 5-6+37-6a-7-8 to 12% of the total transcripts. Similarly, compared to the treatment of 10 μM and 30 μM of ASO-6s, the proportions of isoform 5-6+37-7-8 decreased form 27% to 0% and the proportions of isoform 5-7-8 increased form 64% to 90%, but the proportions of isoform 5-6+37-6a-7-8 increased form 8% to 11%.

This present invention also designed an ASO-AA which hybridization targeting to downstream exonic splicing silencer (ESS) of wrong splicing site (+38 cryptic splice site).

Figure 3F:
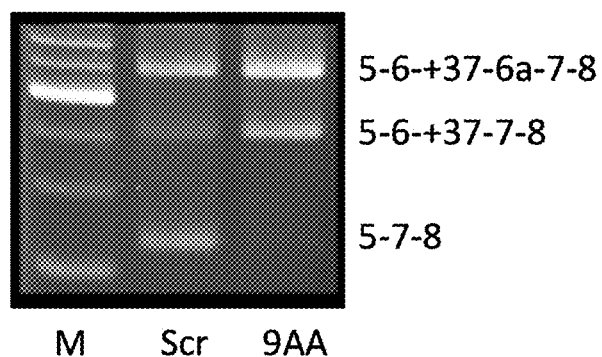
FIG. 3F is a represented electrophoresis gel photograph shows mRNA isoforms in the IVS6+4 A>T mutant cells after treatment of ASOs, wherein identified positions of possible isoforms between DDC gene 5 to 8.
Figure 3G:
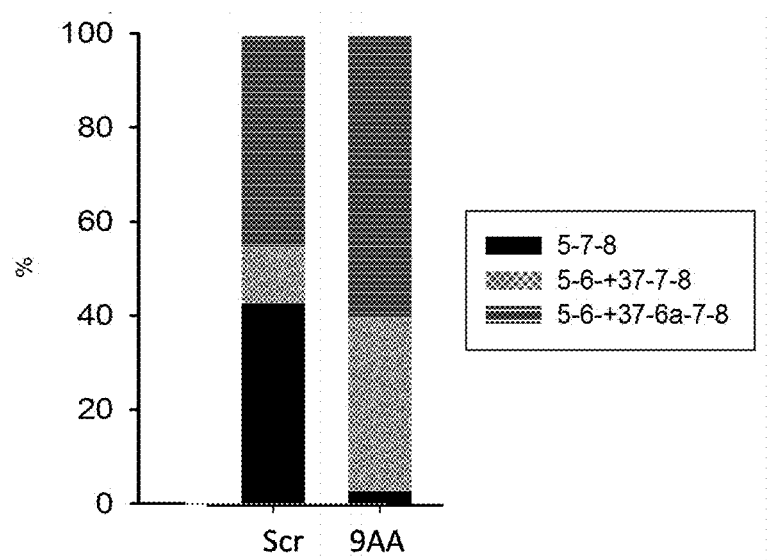
FIG. 3G is quantification of FIG. 3F.

Results from Experiment 1 to 3 were shown at FIG. 3F, 3G. Compared to the treatment of scramble control (Scr), 30 μM ASO-9AA could decrease the proportions of isoform 5-7-8 form 43% to 3% and increase the proportions of isoform 5-6+37-7-8 form 11% to 37%, also increase the proportions of isoform 5-6+37-6a-7-8 form 45% to 59%.

Result 5: SR Proteins SRp30c and SRp55 Modulate the Inclusion of Aberrant Splice Exon 6+37

This present invention designed class 4 ASOs for translation blocking of gene splice trans-acting factors to knockdown SR proteins. Blocking ASOs of TB30, TB40 and TB55 were designed with complementary sequence of mRNA of SRp30c, SRp40, and SRp55 respectively.

Figure 4A:
FIG. 4A is a represented photograph shows protein expression in the IVS6+4 A>T mutant cells after treatment of ASOs, wherein identified the position and strength of SRp30, SRp40 and SRp55 on the western blot membrane.
Figure 4B:
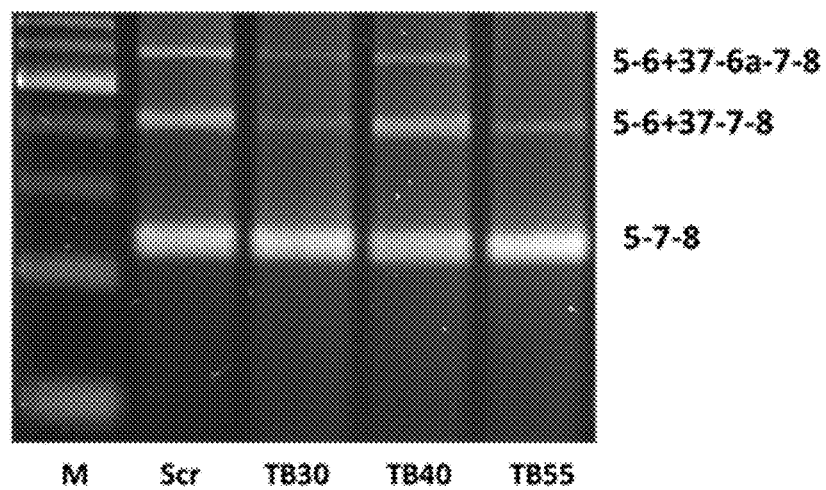
FIG. 4B is a represented electrophoresis gel photograph shows mRNA isoforms in the IVS6+4 A>T mutant cells after treatment of ASOs, wherein identified positions of possible isoforms between DDC gene 5 to 8.
Figure 4C:
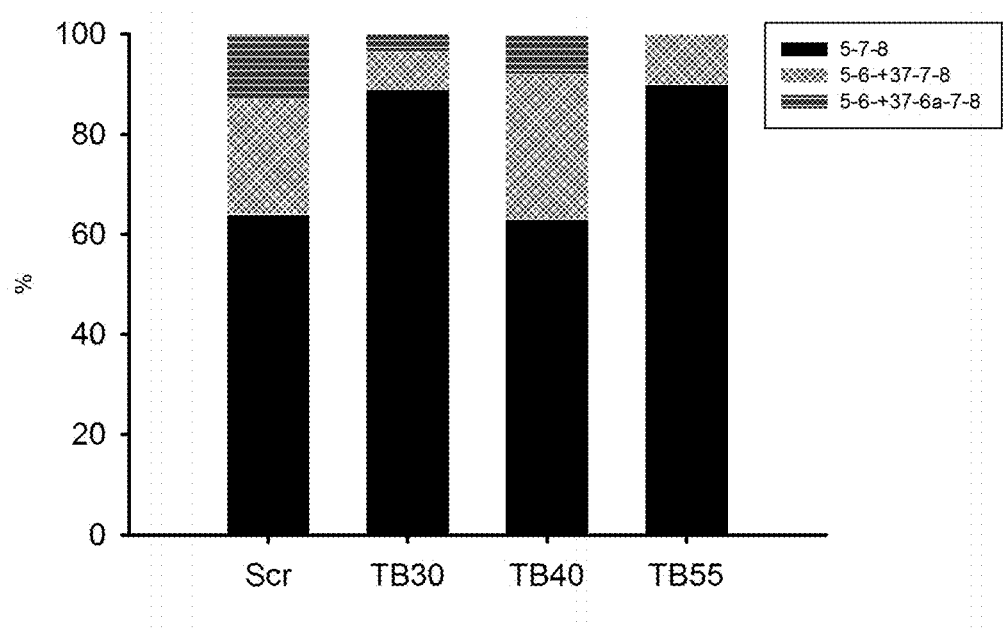
FIG. 4C is quantification of FIG. 4B.

Results from Experiment 1 to 4 were shown at FIG. 4A. Compared to the IVS6+4A>T mutant cells without blocking ASOs treatment, each treatment of 30 μM TB30, TB 40 and TB 55 reduced the levels of SRp30c, SRp40 and SRp55 by approximately 50% respectively, wherein actin in these cells was a reference with no effect of TB30, TB40 and TB55. Referring to FIGS. 4B and 4C, compared with the scramble control (Scr), the treatment of TB30 decreased the proportions of isoform 5-6+37-7-8 in IVS6+4A>T mutant cells form 23% to 7.4%, and increased the proportions of isoform 5-7-8 form 64% to 89%. In TB55 treatment of IVS6+4A>T mutant cells, the proportions of isoform 5-6+37-7-8 decreased form 23% to 9%, and the proportions of isoform 5-7-8 increased form 64% to 90%. The proportions of each isoforms remained approximately the same after treatment of TB40.

Figure 5A:
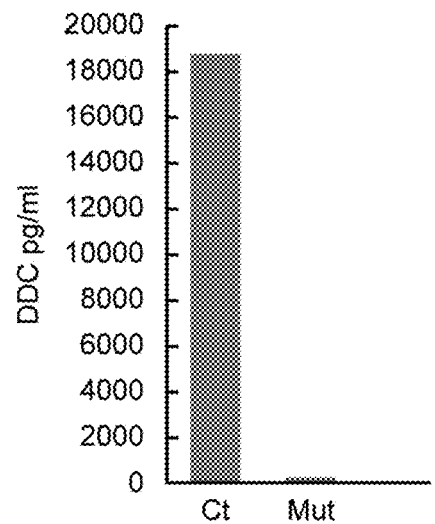
FIG. 5A is DDC protein expression of IVS6+4 A>T mutant cells (Mut) and normal cells (Ct).
Figure 5B:
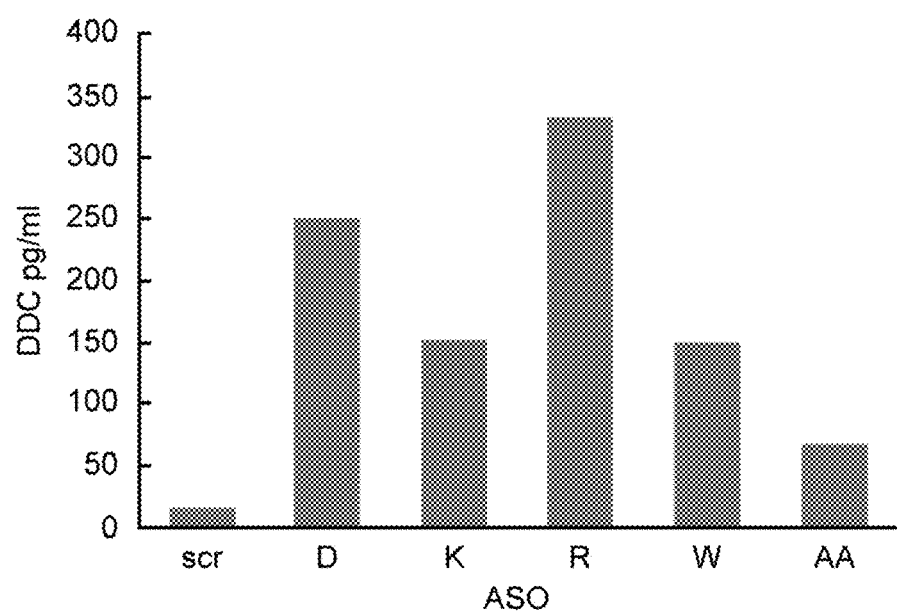
FIG. 5B is DDC protein expression of IVS6+4 A>T mutant cells after treatments of different ASOs.

Result 6: Treatment with ASOs Increased the Level of DDC Protein and Serotonin in Lymphoblastoid Cells Derived from AADC Deficiency Patients with IVS6+4A>T Mutation In order to verified the level and activity of DDC protein would increase effectively after treatment of ASOs. Experiment 5 and 6 were proceeded to identify the level of DDC protein and serotonin, the downstream product. As shown in FIG. 5A, compared with IVS6+4A>T mutant cells (257.4 pg/ml), normal lymphoblastoid cells had high level of DDC protein (18861.7 pg/ml). As shown in FIG. 5B, compared with the level of DDC protein in the control group (17.1 pg/ml), it increased respectively to 252.8, 154.4, 335.4, 151.5 and 69.4 pg/ml after treatment of ASO-D, ASO-K, ASO-R, ASO-W and ASO-AA.

Figure 6A:
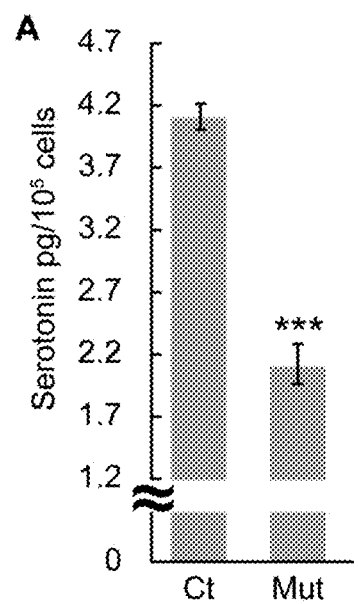
FIG. 6A is serotonine expression of IVS6+4 A>T mutant cells (Mut) and normal cells (Ct).
Figure 6B:
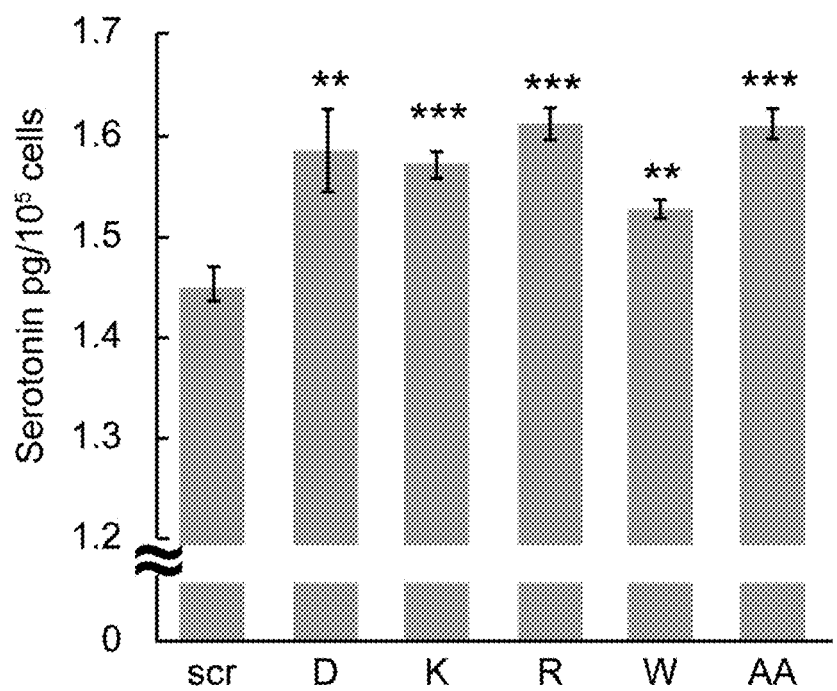
FIG. 6B is serotonine expression of IVS6+4 A>T mutant cells after treatments of different ASOs.

Serotonin levels were identified by ELISA analysis, results were shown as FIG. 6A. Normal lymphoblastoid cells contained significantly higher amounts of serotonin (4.108±0.096 pg/$10^5$ cells) than untreated IVS6+4A>T mutant cells (2.133±0.164 pg/$10^5$ cells) (P<0.001). However, transfection of IVS6+4A>T mutant cells with the ASOs resulted in marked increases in serotonin levels. Treatment with ASO-D, ASO-K, ASO-R, ASO-W, and ASO-AA resulted in increasing of serotonin up to 1.588±0.042, 1.575±0.011, 1.612±0.015, 1.528±0.009, and 1.614±0.014 pg/$10^5$ cells, respectively, compared to that observed for the scramble control cells (1.453±0.018 pg/$10^5$ cells) (P<0.01 for each).

Result 7: In Silico Predictions with the Binding Site and Strength of Splice Regulatory Proteins and DDC Gene In order to understand the binding site of knockout SR protein on DDC gene, in silico predictions with the binding site and strength of splice regulatory proteins and DDC gene were proceeded, wherein SR protein is a kind of splice regulatory protein.

Figure 7A:
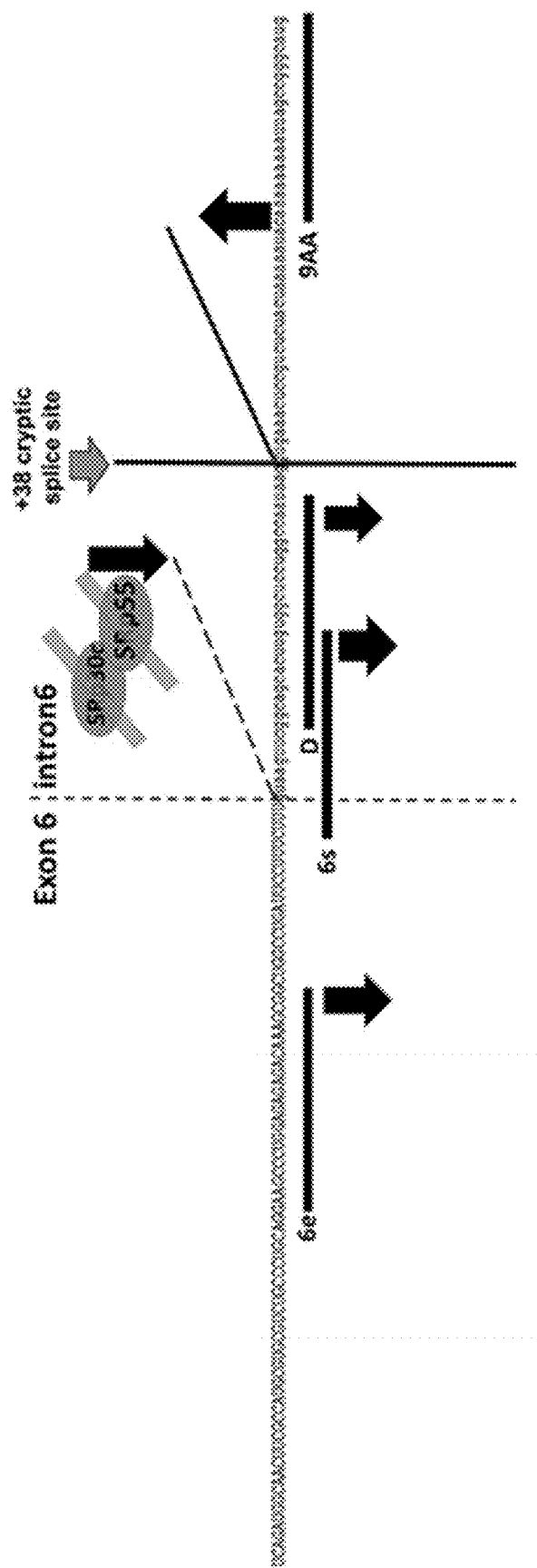
FIG. 7A is the effect of every ASOs designed in this present invention to wrong splice site (+38 cryptic splice site).
Figure 7B:
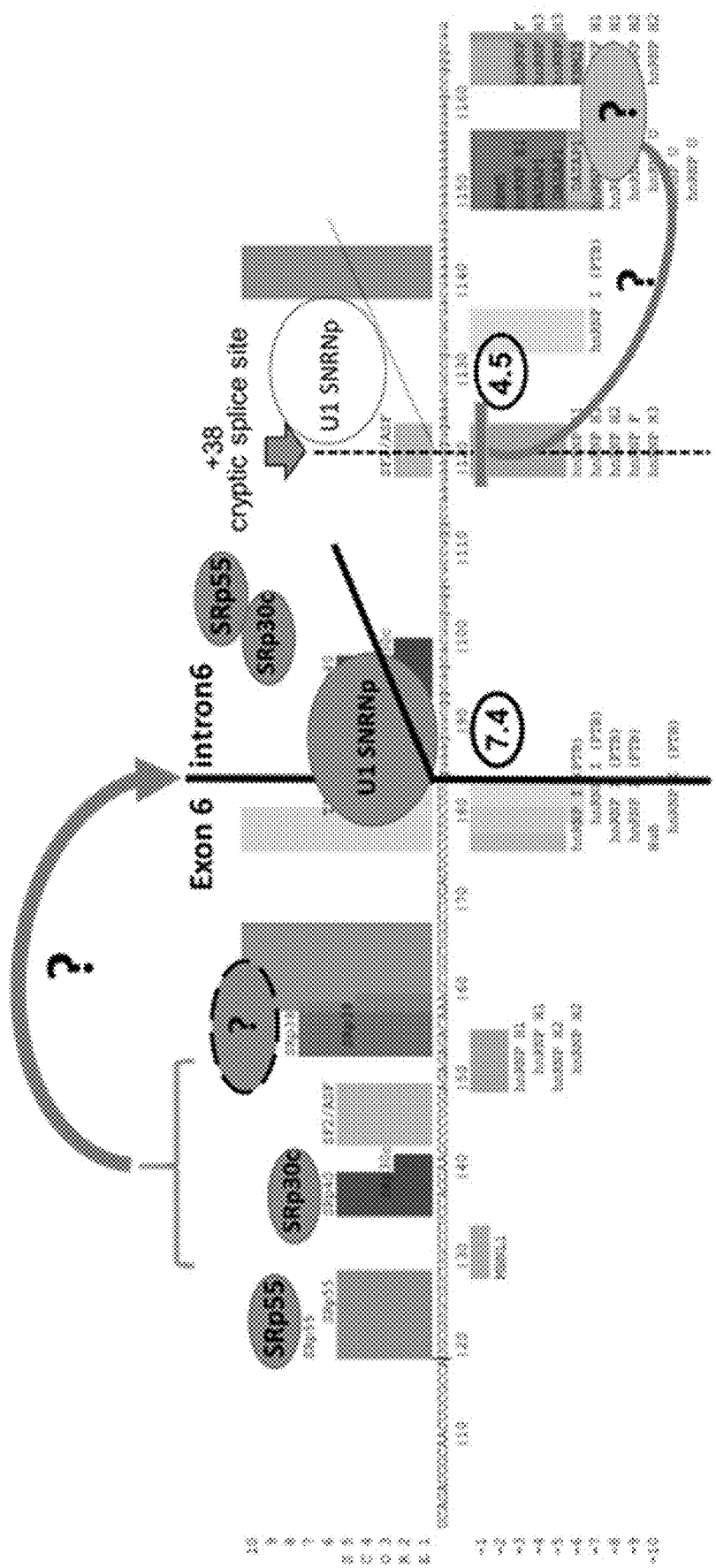
FIG. 7B is in silico predictions of all factors effecting the alternative splice pattern of normal DDC gene.
Figure 7C:
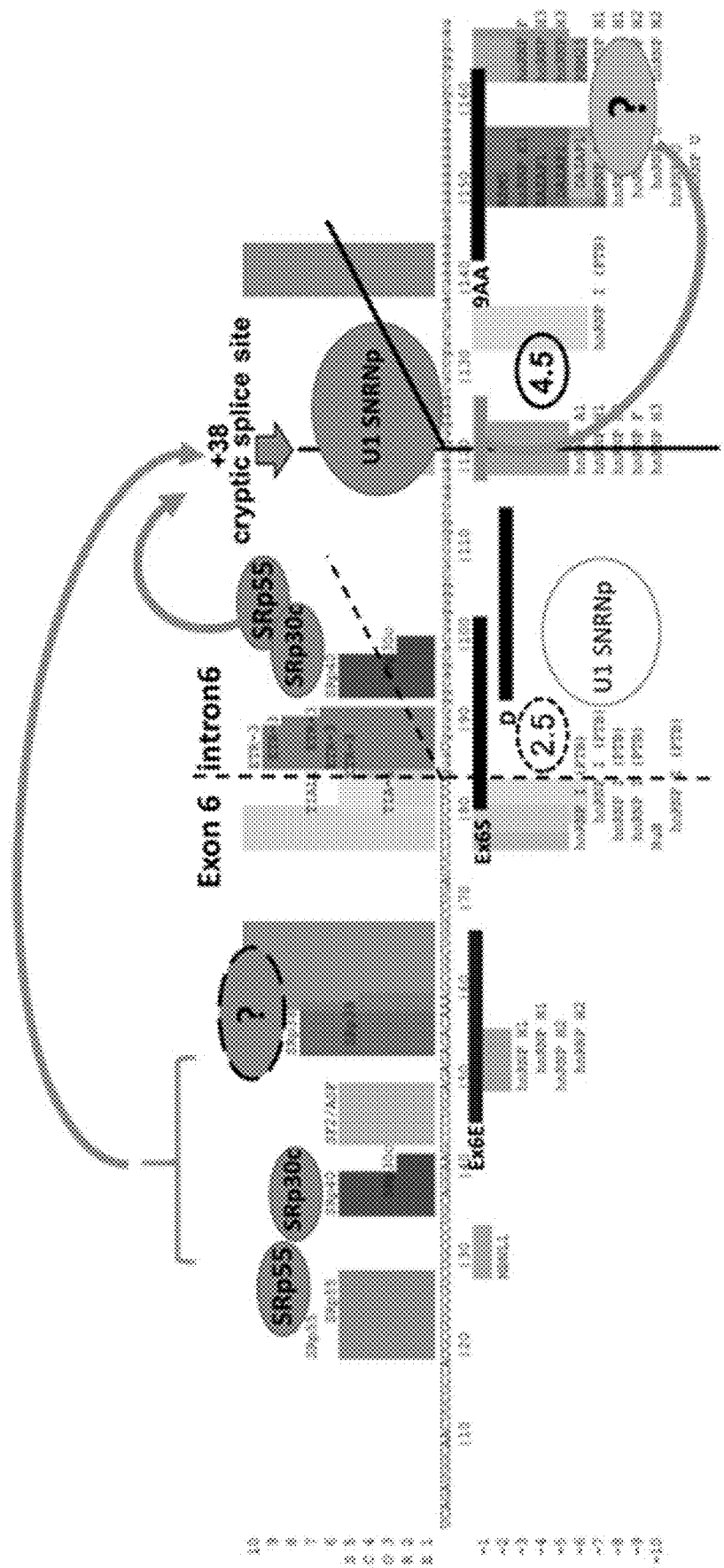
FIG. 7C is in silico predictions of all factors effecting the alternative splice pattern of IVS6+4 A>T mutant DDC gene.

The location of these colorful columns in FIG. 7B, 7C represent the binding site on DDC gene, wherein the upward colorful columns means enhancing gene splicing and the downward colorful columns means inhibiting gene splicing. FIG. 7B is prediction of normal DDC gene. It reveals that besides SRp30c, SRp55, a small nuclear ribonucleoproteins U1 SNRNp would bind on 5' splice site of intron 6 to help normal gene splicing. FIG. 7C is prediction of DDC gene with IVS6+4A>T mutant. It reveals that U1 SNBNp does not bind to the original site, but binds to a wrong splice site (+38 cryptic splice site). SRp30c and SRp55 are binding close to 5' splice site of intron 6, the most distance location was downstream −45 from the 5' splice site of intron 6, as well as upstream+20 from the 5' end of exon 6. Black bar means the binding site for other ASOs on IVS6+4A>T mutant DDC gene. For example, ASO-6e binding site is a binding site for a kind of SR protein (the blue oval within a question mark in the figure). The effect of modulation splicing of ASO-6e may be the result of blocking said kind of SR protein. Another example, ASO-6s and ASO-D binding site is SRp30c and SRp55 binding site. The effect of modulation splicing of ASO-6s and ASO-D may be the result of blocking SRp30c and SRp55.

Notably, ASO-9AA may block many inhibitory splice regulation proteins (the yellow oval within a question mark in the figure). These inhibitory splice regulation proteins are binding between downstream+65 to +86 from the 5' splice site of intron 6 of IVS6+4A>T mutant DDC gene. As shown at FIG. 9, ASOs designed in this present invention cover upstream+324 to downstream −45 from the 5' splice site of intron 6 of IVS6+4A>T mutant DDC gene (SEQ ID NO: 1). Each one of these ASO can hybridize with sequence between downstream+324 to upstream −45 from the 5' splice site of intron 6 of IVS6+4A>T mutant DDC gene (SEQ ID NO: 1) to block splice regulatory protein and result in the effect of adjusting gene splicing.

In conclusion, this present invention designed four class of ASOs to adjust splicing of IVS6+4A>T mutant DDC gene, all locations and sequences of these revealed ASOs are shown at FIG. 9. Referring to FIGS. 7A and 9 together, class 1 ASOs includes ASO-A to ASO-AA and ASO-9AA, which have complementary sequence between downstream+4 to +84 from the 5' splice site of intron 6 of DDC gene. Class 2 ASOs includes ASO-6as and ASO-6ae, which hybridize with new intron 6a as target. Class 3 includes ASO-6e and ASO-6s, which hybridize with exon 6+37 as target. Class 4 includes TB30 and TB55, which have complementary sequence of mRNA of SR protein 30c, SR protein 55. Arrows in FIG. 7A means the probability of wrong splicing site (+38 cryptic splice site) being used. An arrow up means increasing, an arrow down means inhibiting.

In silico predictions can modulate the hybridizing site of gene splicing protein and normal DDC gene (FIG. 7B), and the hybridizing site of gene splicing protein and IVS6+4A>T mutant DDC gene. It can be discovered that SR protein knocked by class 4 ASOs can combine between exon 6 to intron 6. Considering experiment results of class 2 ASOs, if there is a new exon 6a before exon 7, ASOs designed by this present invention can also adjust of that new exon 6a. Therefore, this present invention can adjust ASOs from IVS6+4A>T mutant DDC gene and sequence with downstream+324 to upstream −45 from the 5' splice site of intron 6 of IVS6+4A>T mutant DDC gene (SEQ ID NO: 1).

The above detailed description, which is supported by drawings, is merely intention to provide an embodiment illustrative of the technical content and features of the present invention. The appended claims shall cover simple modifications, replacements or component reduction made, without going against the spirit embodied in the present invention, by persons skilled in the art after gaining insight into the technical content and features of the present invention.

What is claimed is:

1. A synthetic single stranded antisense oligonucleotide comprising at least one chemically modified phosphodiester bond for splicing adjustment of mutant dopa decarboxylase gene which is 84% to 100% complementary to nucleotides 1-101 or nucleotides 319-369 of SEQ ID NO: 1,
   wherein the sequence of the oligonucleotide is selected from one of SEQ ID NOs: 2, 3, 4, 5, or 6.

2. A synthetic single stranded antisense oligonucleotide comprising at least one chemically modified phosphodiester bond for splicing adjustment of mutant dopa decarboxylase gene which is 84% to 100% complementary to nucleotides 1-101 or nucleotides 319-369 of SEQ ID NO: 1, wherein the sequence of the oligonucleotide is selected from one of SEQ ID NO: 7 and 8.

3. A synthetic single stranded antisense oligonucleotide comprising at least one chemically modified phosphodiester bond for splicing adjustment of mutant dopa decarboxylase gene which is 84% to 100% complementary to nucleotides 1-101 or nucleotides 319-369 of SEQ ID NO: 1,
   wherein the sequence of the oligonucleotide is selected from one of SEQ ID NO: 10, 11, 12, and 14.

4. A method of using an antisense oligonucleotide for splicing adjustment of mutant dopa decarboxylase gene by adding the antisense oligonucleotide from claim 1 to IVS6+4A>T mutant cells for cultivation.

* * * * *

SEQUENCE LISTING

```
<160> NUMBER OF SEQ ID NOS: 36

<210> SEQ ID NO 1
<211> LENGTH: 369
<212> TYPE: DNA
<213> ORGANISM: Homo sapiens

<400> SEQUENCE: 1
gaagccctgg agagagacaa agcggctggc ctgattcctt tctttgtaag ttcggcagca      60
cttgtggctc ctggccaata aggtgaaact ccgtctctac taaaaataca aaaaaaaatt     120
agccgggcat ggtggcgcat tcttgtaatc ccagctactc gggaagctga ggcaggagaa     180
tggcgtgaac ccgggaggcg gaggttgcag tgagccgaga tcgcgccgct gcactccagc     240
```

-continued

```
ctgtgtgaca gagcaagact ctgtctcaaa aaaaattaat ctttgagaaa cgcttttac      300 ctccattttt tttttgttt tgtcaattca agtcaattcc acagtgtaat gtggaagaac      360
tgacatggc                                                              369
```

```
<210> SEQ ID NO 2
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 2
ttggccagga gccacaagtg ctgcc                                            25
```

```
<210> SEQ ID NO 3
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 3
caccttattg gccaggagcc acaag                                            25
```

```
<210> SEQ ID NO 4
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 4
ggagtttcac cttattggcc aggag                                            25
```

```
<210> SEQ ID NO 5
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 5
gagacggagt ttcaccttat tggcc                                            25
```

```
<210> SEQ ID NO 6
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 6
agtagagacg gagtttcacc ttatt                                            25
```

```
<210> SEQ ID NO 7
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 7
tgtggaattg acttgaattg acaaa                                            25
```

```
<210> SEQ ID NO 8
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 8
gccatgtcag ttcttccaca ttaca                                              25

<210> SEQ ID NO 9
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 9
caccatgccc ggctaatttt ttttt                                              25

<210> SEQ ID NO 10
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 10
ccgctttgtc tctctccagg gcttc                                              25

<210> SEQ ID NO 11
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 11
acaagtgctg ccgaacatac aaaga                                              25

<210> SEQ ID NO 12
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 12
gctcgtccgc ccagcccgac atc                                                23

<210> SEQ ID NO 13
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 13
cgatgaatac ccgacagcca ctcat                                              25

<210> SEQ ID NO 14
<211> LENGTH: 25
<212> TYPE: DNA
<213> ORGANISM: Artificial Sequence
<220> FEATURE:
<223> OTHER INFORMATION: antisense oligonucleotide
```

```
<400> SEQUENCE: 14
acccaagggc tggttgtcga acggc                                         25

<210> SEQ ID NO 15
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 15
aagccgtcgt gaacaccgag gaccg                                         25

<210> SEQ ID NO 16
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 16
agccgtcgtg aacaccgagg accgg                                         25

<210> SEQ ID NO 17
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 17
gccgtcgtga acaccgagga ccggt                                         25

<210> SEQ ID NO 18
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 18
cgtcgtgaac accgaggacc ggtta                                         25

<210> SEQ ID NO 19
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 19
gtcgtgaaca ccgaggaccg gttat                                         25

<210> SEQ ID NO 20
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 20
tcgtgaacac cgaggaccgg ttatt                                         25

<210> SEQ ID NO 21
<211> LENGTH: 25
```

```
<212> TYPE: DNA
<213> ORGANISM: Artificial Sequence
<220> FEATURE:
<223> OTHER INFORMATION: antisense oligonucleotide

<400> SEQUENCE: 21
cgtgaacacc gaggaccggt tattc                                            25

<210> SEQ ID NO 22
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 22
gtgaacaccg aggaccggtt attcc                                            25

<210> SEQ ID NO 23
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 23
tgaacaccga ggaccggtta ttcca                                            25

<210> SEQ ID NO 24
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 24
aacaccgagg accggttatt ccact                                            25

<210> SEQ ID NO 25
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 25
acaccgagga ccggttattc cactt                                            25

<210> SEQ ID NO 26
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 26
caccgaggac cggttattcc acttt                                            25

<210> SEQ ID NO 27
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 27
```
accgaggacc ggttattcca ctttc                                          25

<210> SEQ ID NO 28
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 28
ccgaggaccg gttattccac tttca                                          25

<210> SEQ ID NO 29
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 29
cgaggaccgg ttattccact ttcag                                          25

<210> SEQ ID NO 30
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 30
aggaccggtt attccacttt caggc                                          25

<210> SEQ ID NO 31
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 31
ggaccggtta ttccactttc aggca                                          25

<210> SEQ ID NO 32
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 32
gaccggttat tccactttca ggcag                                          25

<210> SEQ ID NO 33
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 33
accggttatt ccactttcag gcaga                                          25

<210> SEQ ID NO 34
<211> LENGTH: 25
<212> TYPE: DNA
<213> ORGANISM: Artificial Sequence

```
<220> FEATURE:
<223> OTHER INFORMATION: antisense oligonucleotide

<400> SEQUENCE: 34
cggttattcc actttcaggc agaga                                    25

<210> SEQ ID NO 35
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 35
ggttattcca ctttcaggca gagat                                    25

<210> SEQ ID NO 36
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 36
gttattccac tttcaggcag agatg                                    25
```